US005579583A

United States Patent [19]
Mehregany et al.

[11] Patent Number: 5,579,583
[45] Date of Patent: Dec. 3, 1996

[54] MICROFABRICATED BLADES

[75] Inventors: Mehran Mehregany, Shaker Heights, Ohio; Randal H. Rudderman, Norcross, Ga.; Robert L. Mullen, Moreland Hills, Ohio

[73] Assignee: MicroMed, Incorporated, Duluth, Ga.

[21] Appl. No.: 375,243

[22] Filed: Jan. 19, 1995

Related U.S. Application Data

[63] Continuation of Ser. No. 208,915, Mar. 9, 1994, abandoned, which is a continuation of Ser. No. 949,099, Sep. 22, 1992, abandoned.

[51] Int. Cl.$^6$ ................................ B26B 3/00; B25G 3/00
[52] U.S. Cl. ........................ 30/342; 30/355; 606/167
[58] Field of Search ........................ 30/350, 346.54, 30/346.53, 355, 342; 606/167

[56] References Cited

U.S. PATENT DOCUMENTS

| | | | |
|---|---|---|---|
| 3,857,488 | 12/1974 | LeCren | 177/60 X |
| 3,894,337 | 7/1975 | Jones | 30/346.54 |
| 4,091,813 | 5/1978 | Shaw et al. | 30/140 X |
| 4,409,659 | 10/1983 | Devine | 228/110 X |
| 4,534,827 | 8/1985 | Henderson | 252/79.2 X |
| 4,566,465 | 1/1986 | Arhan et al. | 606/192 X |
| 4,697,489 | 10/1987 | Kim | 83/915.5 X |
| 4,719,915 | 1/1988 | Porat et al. | 128/305 |
| 4,790,812 | 12/1988 | Capuano, Sr. et al. | 128/305 |
| 4,798,000 | 1/1989 | Bedner et al. | 30/339 |
| 4,846,250 | 7/1989 | Bedner et al. | 164/47 |
| 4,850,353 | 7/1989 | Stasz et al. | 128/303.14 |
| 4,922,903 | 5/1989 | Welch et al. | 606/37 |

FOREIGN PATENT DOCUMENTS

| | | | |
|---|---|---|---|
| 2536691 | 6/1984 | France | 30/346.54 |
| 3047888 | 7/1982 | Germany | 30/346.54 |
| 0092388 | 4/1990 | Japan | 30/350 |

OTHER PUBLICATIONS

Grieshaber & Co., Inc., Brochure, CA 1990.
Kenneth E. Bean, "Anisotropic Etching of Silicon", IEEE Transactions on Electron Devices, vol. ED-25, No. 10, Oct. 1978, pp. 1185–1193.
Kendall et al., "Orientations of the Third Kind: The Coming of Age of (110) Silicon", Micromachining and Micropackaging of Transucers, Elseiver Science Publishers B.V., Amsterdam, 1985, pp. 107–121.

Primary Examiner—Kenneth E. Peterson
Attorney, Agent, or Firm—Wolf, Greenfield & Sacks, P.C.

[57] ABSTRACT

A micromachined blade suitable for medical applications has an edge which is free of the imperfections common in mechanically sharpened steel blades. A method of forming micromachined blades having the desired characteristics may be performed by etching with anisotropic or isotropic etchants. This micromachined blade may be formed of a single-crystalline substrate, such as a silicon wafer commonly used in integrated circuit technology. Thus, such a micromachined blade may also carry circuitry capable of assisting a surgeon in the performance of certain procedures.

8 Claims, 16 Drawing Sheets

MICROFABRICATED BLADES

This application is a continuation, of application Ser. No. 08/208,915, filed Mar. 9, 1994, now abandoned which was a continuation of application Ser. No. 07/949,099, filed 22 Sep. 1992, now abandoned.

BACKGROUND OF THE INVENTION

1. Field of the Invention

This invention relates to instruments for cutting, and more particularly to blades produced by microfabrication techniques.

2. Discussion of the Prior Art

Conventional blades of steel are well known. Steel blades are used in a wide variety of applications, ranging from non-precision implements such as steak knives to precision implements such as surgical instruments. Surgical blades of steel are manufactured in a variety of shapes, but all share the characteristics that sharpness and precision of the edge are important to the proper functioning of the instrument.

A electron micrograph of one such conventional steel blade is shown at a 5000× magnification in FIG. 1.

As seen in FIG. 1, steel blades manufactured using conventional techniques include numerous minute surface imperfections. These imperfections may result from mechanical sharpening processes or from chemical processes occurring at the surface of the blade, such as corrosion by exposure to the air. As a result, the actual cutting edge 101 of such a blade may have a significant radius, may be quite irregular (though macroscopically appearing smooth) and may vary in sharpness.

As a result of these minute imperfections, a conventional steel surgical blade cannot cut without some tearing of tissue. Such tearing of tissue during surgery may slow down healing, and also may result in scar tissue formation during and after healing is completed.

Certain delicate surgeries such as ophthalmological, cardiovascular and cosmetic procedures are rendered more difficult or yield less satisfactory results due to the problems with conventional steel surgical blades.

Finally, some processes in the manufacture of conventional steel surgical blades do not lend themselves to economical mass production of blades. For example, formation of the blade and sharpening of the cutting edge are typically separate operations. Although the blade may be formed by a precision stamping or die cutting operation, the cutting edge must be ground and honed. Each blade is individually fixtured for these operations, which may then be performed simultaneously on large numbers of blades.

SUMMARY OF THE INVENTION

Accordingly, it is a general aim of the present invention to provide an improved blade, particularly an improved surgical blade which causes a minimum amount of tissue damage during a cut because of superior sharpness, but is very economical to mass produce.

A micromachined blade in accordance with the present invention has a sharp cutting edge, defined at any point along the edge by the intersection of two crystal planes. In one embodiment, the sharp cutting edge may be defined by only two flat, intersecting, crystal planes. Other embodiments employ other geometries, such as piecewise linear, curved geometries, which optimize the cutting edge for various desirable cutting characteristics. In some embodiments a sharp tip may be formed of an intersection of several crystal planes.

A method in accordance with the present invention produces the micromachined blades described above. Such a process may be performed on a wafer of single-crystalline material, such as single-crystal silicon, using isotropic or anisotropic chemical etchants, or other etching technologies. A polished crystal wafer is provided with an etch mask, of a material resistant to the etchant to be employed. This may be done by methods known in the integrated circuit arts, for example by oxidation followed by a standard photolithographic process. Holes are opened in the etch mask, exposing areas of the crystal wafer, where it is desired to remove some or all of the crystal material. The crystal wafer is then exposed to etchant through the holes in the etch mask, thereby removing undesired material.

The micromachined blade of the present invention may be formed of crystalline silicon, such as is commonly used in integrated circuit fabrications. As such, these micromachined blades may also include electronic circuitry to aid in the performance of certain procedures therewith. For example, temperature and strain/stress measurement components, as well as resistive heating elements may be integrated near the cutting edge of the blade. Procedures which may make use of this electronic circuitry may be performed manually, or with the assistance of a computer, or even fully automated.

Micromachined blades according to the present invention may be used as surgical scalpels for any surgery, in particular where the degree of tissue damage is a major issue. Surgical procedures involving the tissues of the eye are such sensitive procedures. Micromachine blades according to the present invention produce less tissue distortion than other blades and therefore there is less probability of tissue necrosis, less scar tissue and better healing.

The blades of the present invention may also be provided with single use or multi-use handles. Designs for such handles may include one part or multi-part constructions.

BRIEF DESCRIPTION OF THE DRAWING

The present invention will be further understood in connection with the accompanying drawing wherein like numerals refer to like elements.

DETAILED DESCRIPTION

A detailed description will now be given of several aspects and embodiments of the present invention.

Figure 1:
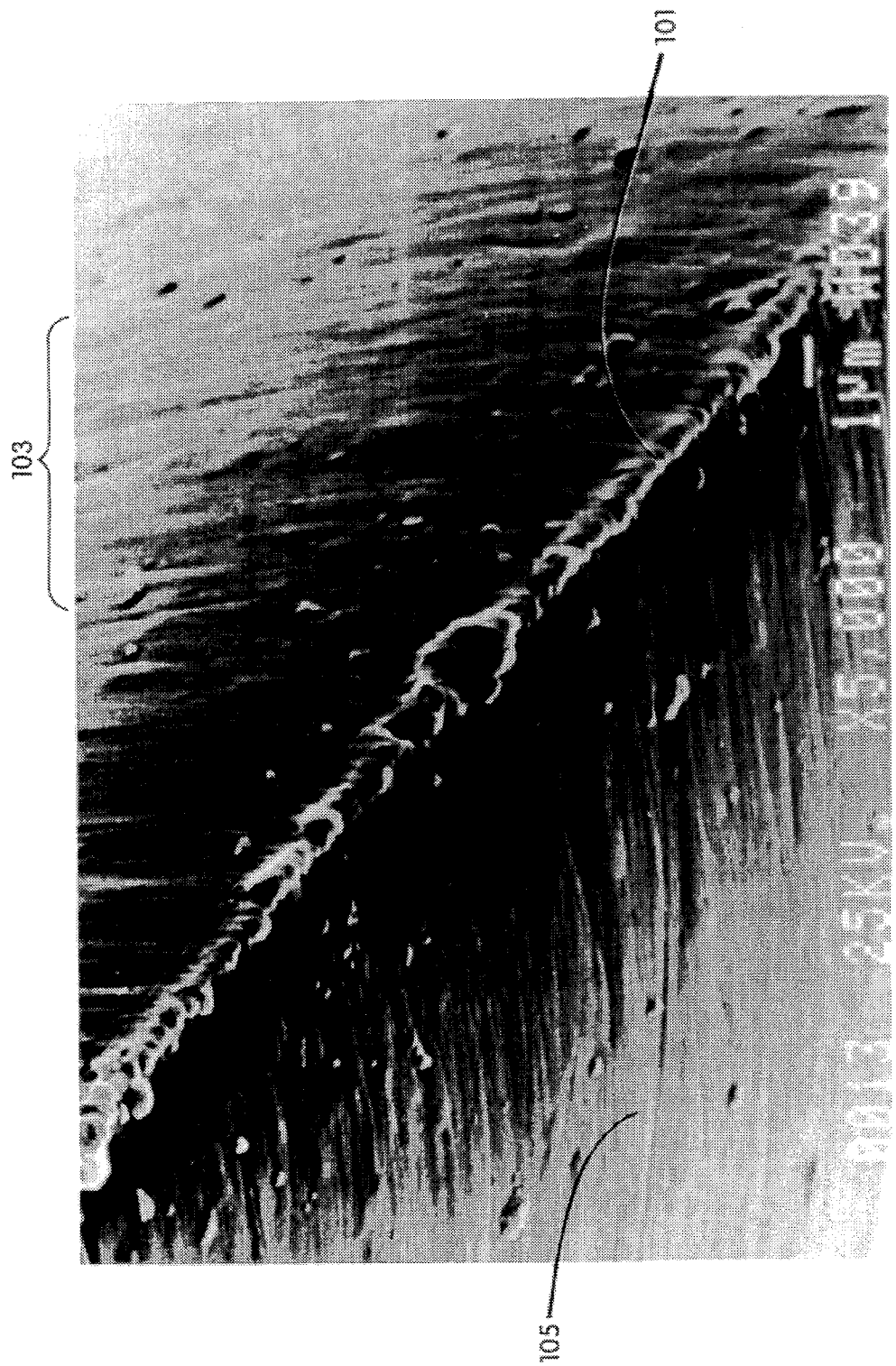
FIG. 1 is a electron micrograph of a cutting edge on a conventional, steel surgical blade.
Figure 2:
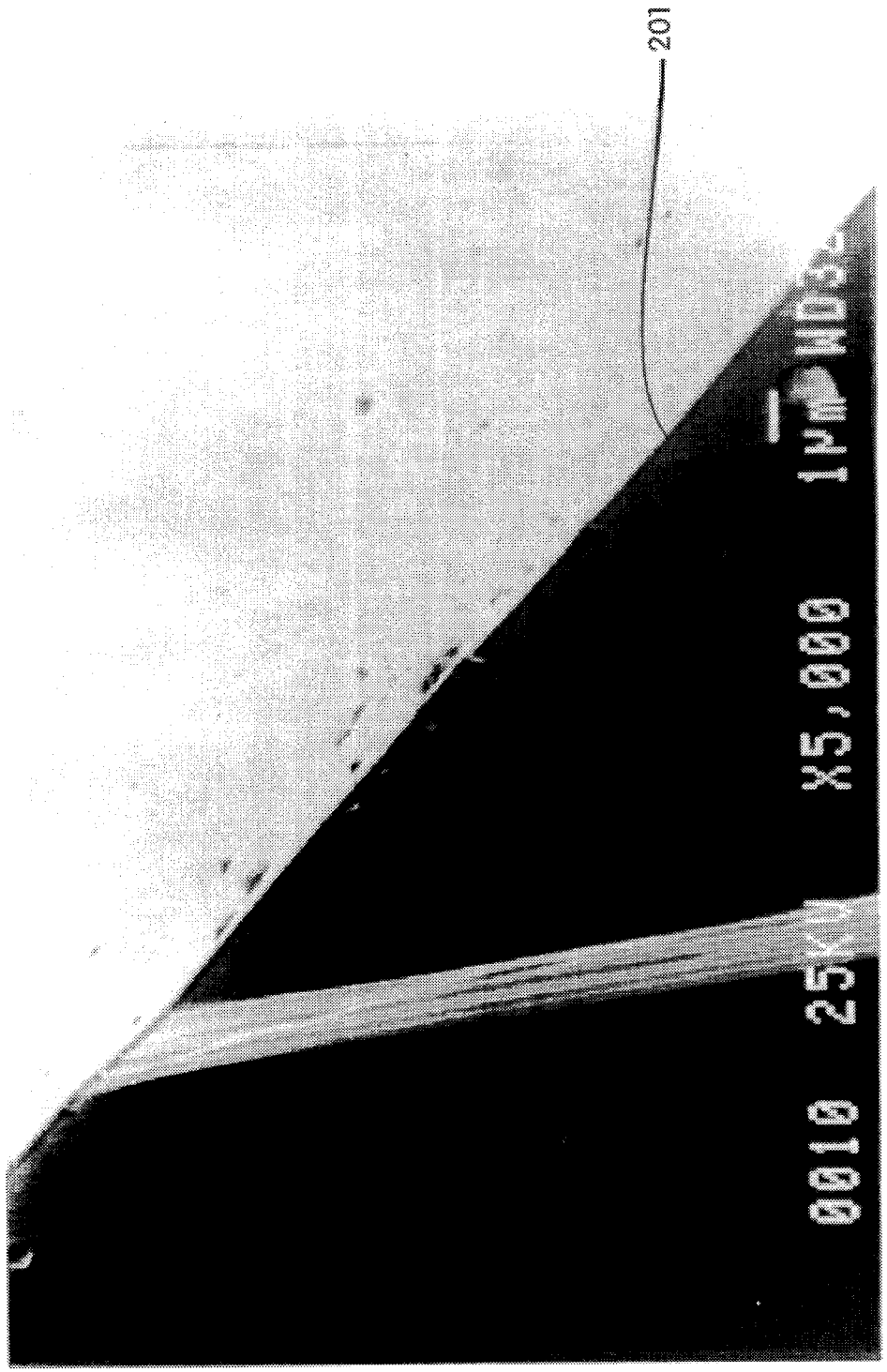
FIG. 2 is a electron micrograph of a cutting edge on a blade according to the present invention.

By comparing the electron micrograph of FIG. 1 with that of FIG. 2, a qualitative difference between the cutting edge 101 of a conventional steel surgical blade and the cutting edge 201 of a blade according to the present invention may be readily seen. While the cutting edge of the conventional blade includes numerous tooling marks (e.g. 103), scratches (e.g. 105) and an imperfectly sharp cutting edge 101, the blade of the present invention does not exhibit these minute imperfections. In fact, the blade of the present invention, as seen in FIG. 2, has a cutting edge whose radius is undetectable, even at a magnification of 5000×. The blade shown was formed from a wafer of single-crystal silicon, although other single-crystal materials are suitable.

Figure 3:
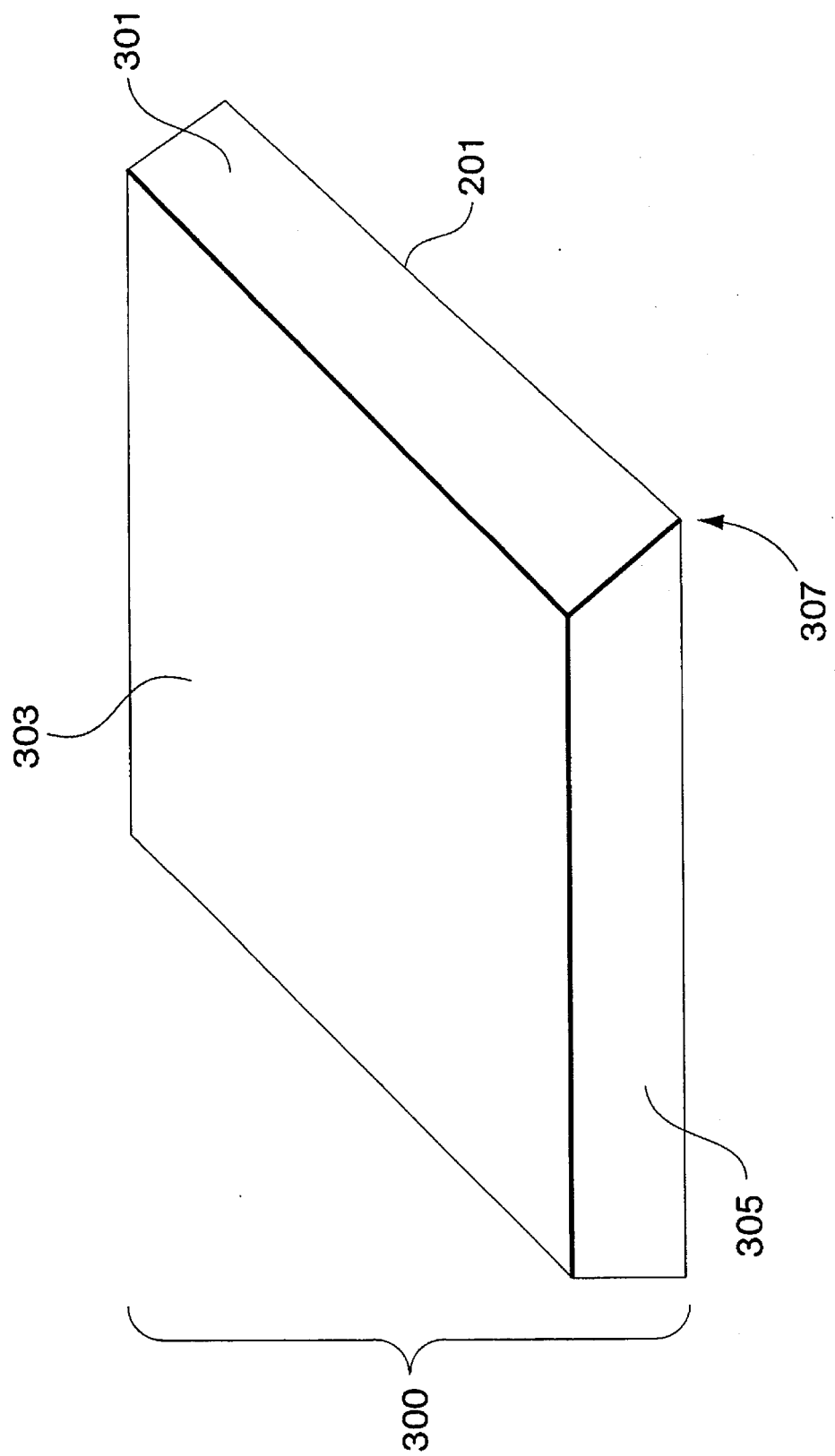
FIG. 3 is a perspective view of a blade according to the present invention.

The structure of the blade shown in FIG. 2 is now described in greater detail, in connection with FIG. 3. The blade body 300 is formed from a wafer of material cut from a single crystal of silicon, as noted above. Since silicon is used commonly in integrated circuit fabrication this offers certain advantages, as will be seen below.

The silicon wafer is cut from a single crystal and polished such that the top and bottom surfaces of the wafer, which will form the top surface 303 of the blade and the bottom surface (not shown) of the blade have crystalographic orientation <100>. A flat surface 301 corresponding to a <111> crystalographic plane forms an acute angle with the bottom <100> plane of the wafer. Thus, a sharp cutting edge 201 is formed at the intersection of flat surface 301 and the bottom surface of the wafer. The front surface 305 and back surface (not shown) of the blade may also be formed coincident with crystalographic planes of the silicon wafer. The corner, or sharp tip 307 formed at each end of sharp cutting edge 201 results from the intersection of three substantially flat, planar surfaces.

A method of fabricating the blade of FIG. 3 is now described in further detail with reference to FIGS. 4A–4H.

Figure 4A:
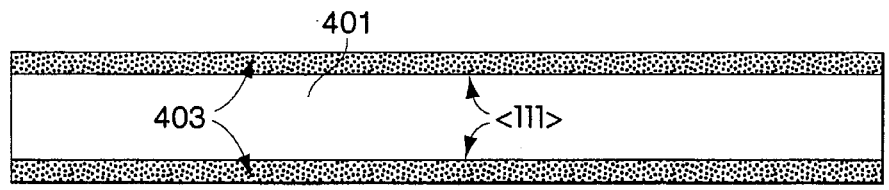
FIGS. 4A–4H are cross sectional views illustrating the fabrication of a blade according to the process of the present invention.
Figure 4B:
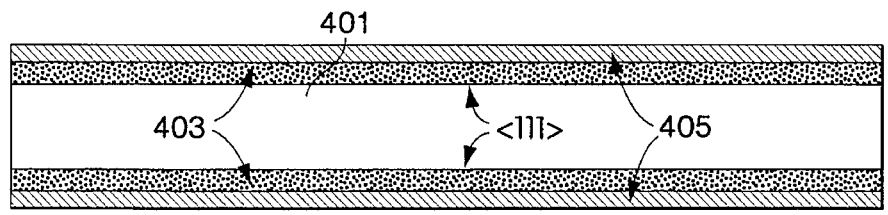
Figure 4C:
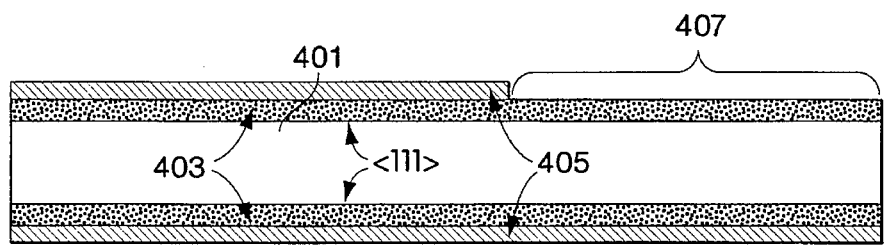
Figure 4D:
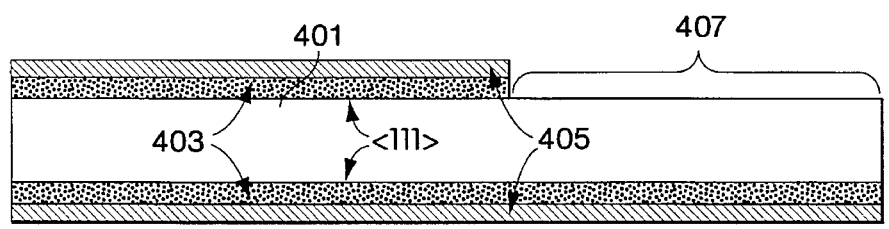
Figure 4E:
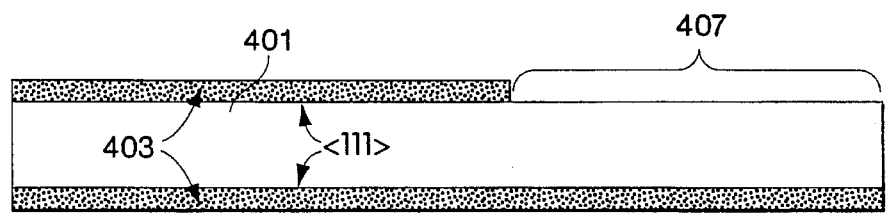

FIGS. 4A–4E show the formation of a patterned silicon etch mask layer. In FIG. 4A a silicon wafer 401 has already been polished and oxidized on both sides to form layers of silicon dioxide 403. Next, the layers of silicon dioxide 403 are coated with layers of photoresist 405, as shown in FIG. 4B. Conventional photolithographic techniques may be used to remove photoresist 405 from a selected area 407, resulting in the structure of FIG. 4C. FIG. 4D illustrates that silicon dioxide 403 is next removed from area 407, to form holes or windows defining the areas of the silicon wafer to be etched. The holes or windows, thus formed, have an edge parallel to a <111> crystal plane, in the <110> direction, which will define cutting edge 101 of the blade. As shown in FIG. 4E the photoresist layers 405 are stripped off prior to etching.

In the process illustrated, the silicon etch mask pattern is formed in the silicon dioxide rather than the photoresist, since silicon dioxide is more resistant to the activity of the silicon etchant than the photoresist. Thus, it will protect from the silicon etchant those areas of the silicon wafer which are to form the body of the blade according to the present invention.

Figure 4F:
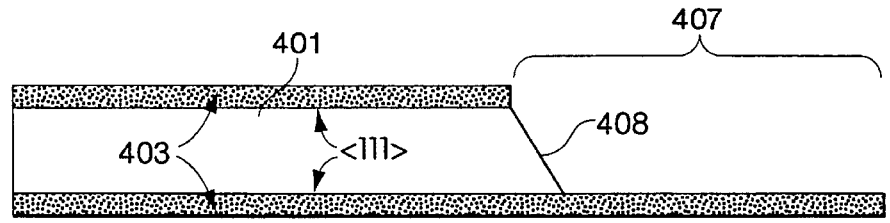
Figure 4G:
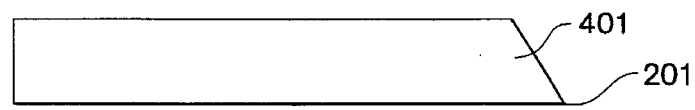

The silicon wafer is next exposed to an anisotropic silicon etchant which preferentially etches the <100> and <110> crystalographic planes, removing material from those planes at a much higher rate than from the <111> planes. Thus, the plane defining the blade edge 408 is formed along a <111> plane as shown in FIG. 4F. The silicon dioxide 403 may then be stripped off as illustrated in FIG. 4G, leaving a micromachined blade having a sharp cutting edge 201.

Figure 4H:

If it is so desired, the blade may be coated with any of a variety of wear-resistant coatings 409, such as silicon nitride, silicon carbide, tungsten carbide or a diamond-like carbon film, as shown in FIG. 4H. Coating deposition may be carried out by silicon microfabrication techniques known in the art, such as chemical vapor deposition.

The method thus described is preferably performed using an anisotropic silicon etchant, such as ethylenediamine and pyrochatecol (EDP), potassium hydroxide, or hydrazine. The silicon etchants listed herein are representative of the anisotropic silicon etchants available, however, many suitable anisotropic silicon etchants are known. The blade illustrated in FIG. 2 was etched using EDP.

Although there are a variety of suitable silicon etchants, a number of parameters affect the selection of preferable silicon etchants. Among these are controllability, etch rate ratio, overall etch rate and safety. As seen in FIG. 2, EDP produces a smooth, high-quality surface. EDP has been found to etch the <100> plane at 50 µm/hr, the <110> plane at 30 µm/hr, and the <111> plane at 3 µm/hr at a temperature of 110° C. Although EDP can be hard to control at temperatures above 100° C., the etch rate ratio of 50:30:3 for <100>:<110>:<111> planes makes it particularly suitable for this application. Furthermore, EDP produces exceptionally high quality surfaces, containing few defects.

The silicon etchants discussed above perform acceptably in a temperature range of 50°–120° C. The blade of FIG. 2 was processed at 110° C., which resulted in a combined etch rate of just over 1 µm/min. For a blade made from a typical 0.2 mm thick wafer, etching thus takes about 200 minutes. The silicon etch mask was a 3000 Å layer of silicon dioxide, thermally grown at 1000° C.

Figure 5A:
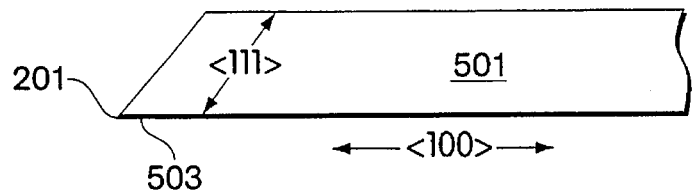
FIGS. 5A–5C are cross sectional views of blades fabricated according to the present invention, using anisotropic etchant.
Figure 5B:
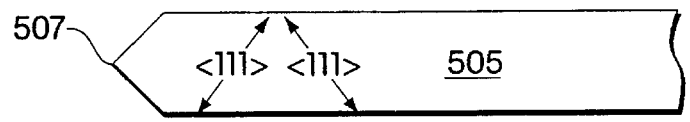
Figure 5C:

A variety of different blade geometries are possible. The edge 201 of the blade 501 of FIG. 5A is of the type also shown in FIGS. 2, 3 and 4A–4G, having an edge defined by the intersection of a <111> plane which has been etched from one side, only, with a surface 503 defined by a <100> plane. However, the silicon etch mask on both the top and bottom surfaces of the wafer may be patterned, resulting in the blades of FIGS. 5B–5C. If the silicon etch mask is patterned symmetrically on both top and bottom surfaces of the wafer, the blade 505 of FIG. 5B may be formed. The edge 507 of this blade 505 is defined by the intersection of two <111> planes. By controlling the duration of etching from each side, and the alignment and size of the etch mask windows, the cutting edge 509 of the blade 511 may be offset, as shown in FIG. 5C.

In silicon, the <111> plane makes an angle of 54.7° with the <100> plane. Thus, in FIG. 5A the sharp cutting edge 201 makes an angle of 54.7°. In FIGS. 5B and 5C, the sharp cutting edges 507 and 509, respectively, are formed by the intersection of two <111> planes, as noted above. Thus, the sharp cutting edges 507 and 509 of these blades 505 and 511, respectively, have angles of 109.4°.

Figure 6A:
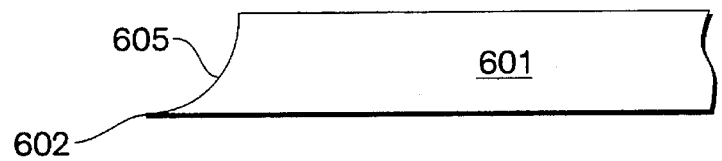
FIGS. 6A–6B are cross sectional views of blades fabricated according to the present invention, using isotropic etchant.
Figure 6B:
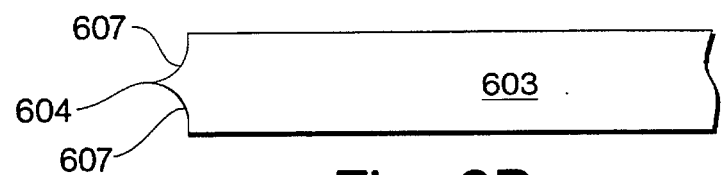

It is also possible to fabricate sharp blades such as 601 and 603 as shown in FIGS. 6A and 6B using isotropic etching of silicon. In such embodiments, either single-crystal or polycrystaline materials may be used. Very sharp edges (602 and 604, corresponding with blades 601 and 603, respectively) with narrow angles of attack are possible using this technique. However, process control is more complicated than for that of anisotropic etching. Typical isotropic silicon etchants that may be used in this technique are ternary mixtures of HF, $HNO_3$ and $CH_3COOH$. Silicon dioxide and silicon nitride are candidates for the patterned silicon etch mask layer.

The blades 601 and 603 of FIGS. 6A and 6B, respectively have curved profiles 605 and 607, respectively, since isotropic etching produces an inverse relationship between the distance from the surface and the amount of material removed. Blade 601 of FIG. 6A is produced by etching a silicon wafer from one side only, whereas blade 603 of FIG. 6B results from etching a silicon wafer from both sides. The process of fabricating these blades includes the same steps as described above, but using an isotropic silicon etchant for the step of etching.

Figure 7A:
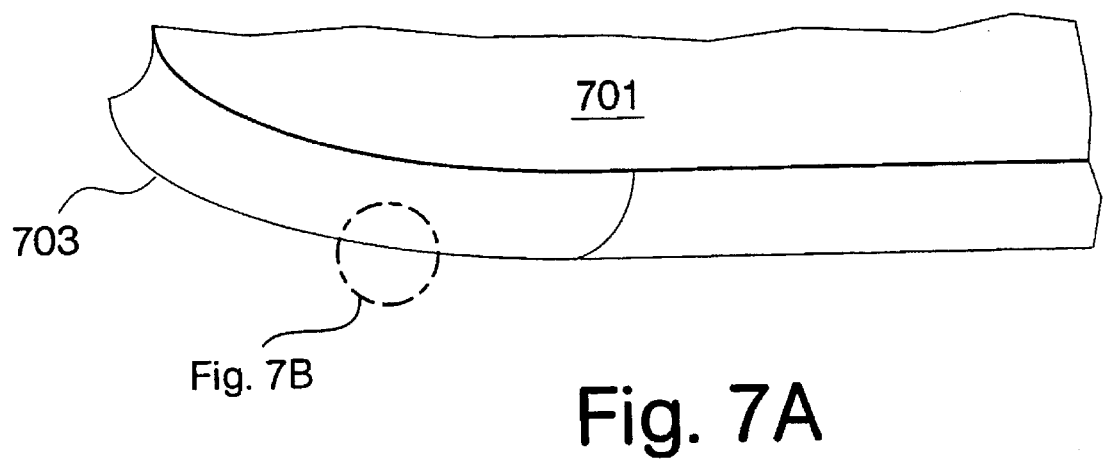
FIGS. 7A–7C are perspective views of a blade fabricated according to the present invention, and having a curved cutting edge.
Figure 7B:
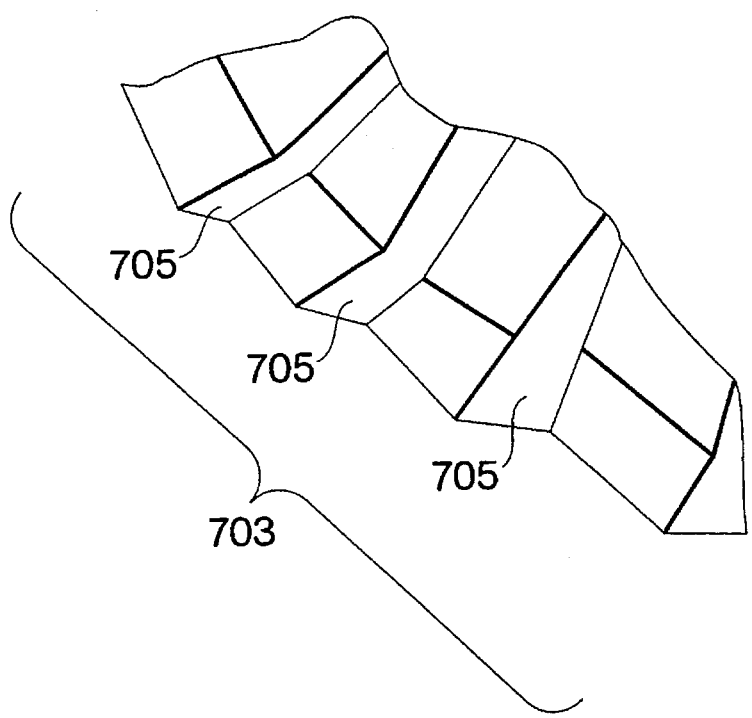
Figure 7C:
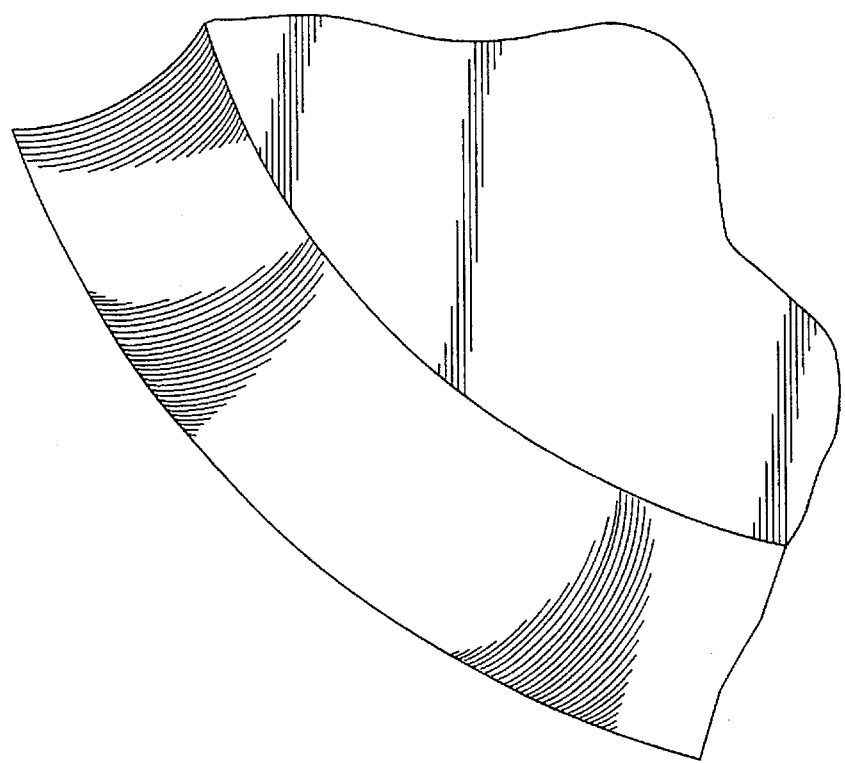

A blade 701 according to the present invention, having a curved sharp cutting edge 703 is shown in FIGS. 7A, 7B and 7C. Such blades are formed by defining the curved edge in the silicon etch mask pattern of the process described above. Instead of defining windows with one edge parallel to the <111> crystal plane, the window would have an edge defining the desired curvature. FIG. 7B shows the result of using anisotropic silicon etchant to form the blade, while FIG. 7C shows the result of using isotropic silicon etchant to form the blade.

Although each point along sharp cutting edge 703 of the blade of FIG. 7B is formed by the intersection of only two crystal planes, the macroscopic curve of the cutting edge 703 results in microscopic discontinuities 705 where higher-index crystal planes are crossed by the line of the cutting edge 703. This should be one of the factors considered during the selection of a particular blade for a particular procedure.

As seen in FIG. 7C, the use of isotropic silicon etchant results in a blade having a smoothly curved cutting edge. The profile and sharpness of this blade is comparable to that illustrated in FIG. 6A.

Figure 8:
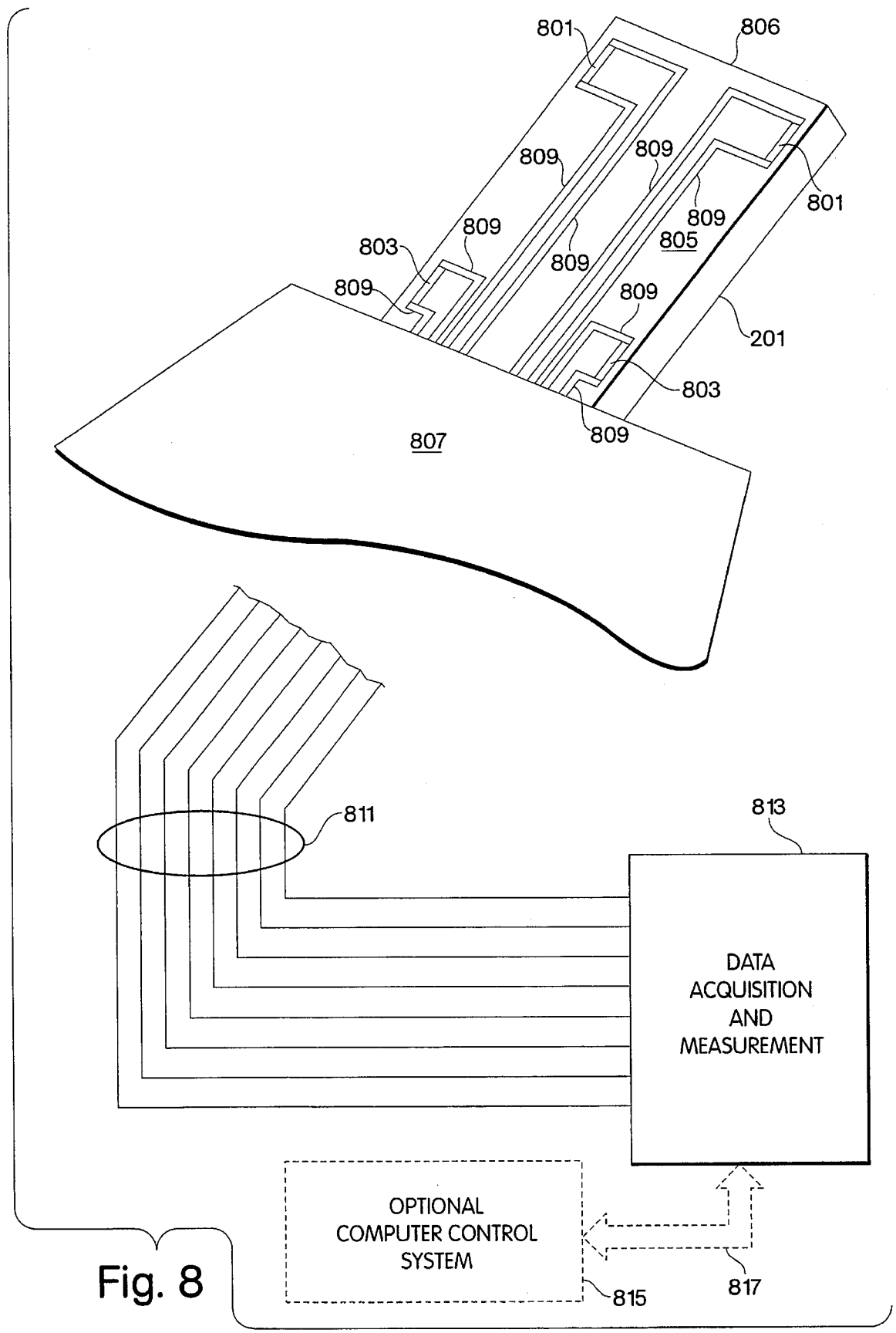
FIG. 8 is a combined perspective view of a blade fabricated with resistors integrated at various locations on the blade and system block diagram of a system for using such a blade.
Figure 9:
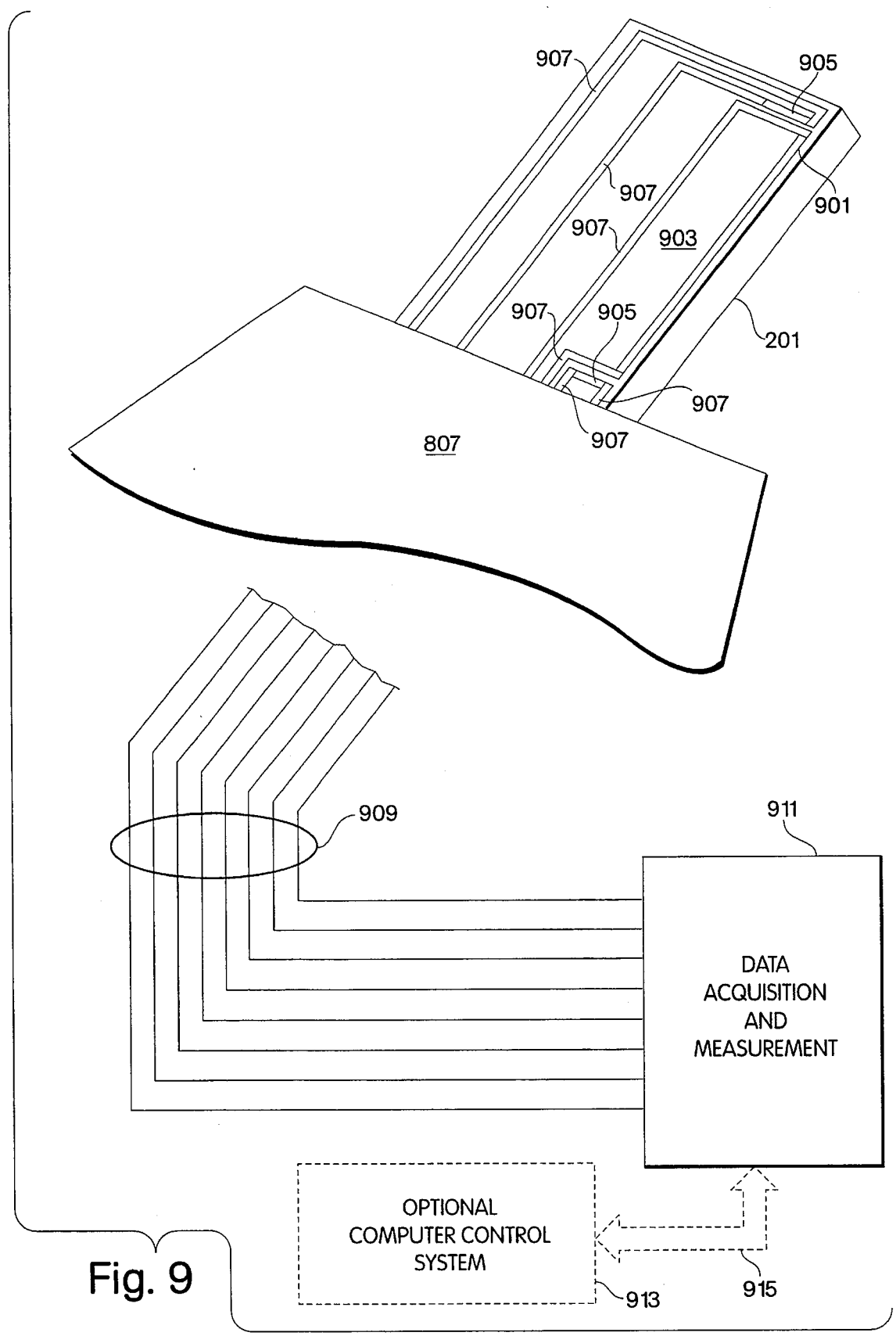
FIG. 9 is a combined perspective view of a blade fabricated with a heating element integrated at one edge and system block diagram of a system for using such a blade.

Silicon-based embodiments of the present invention may include electronic circuitry on them, as shown in FIGS. 8 and 9. Such blades could assist a surgeon in accomplishing a desired procedure. This is possible since the processing technology used to micromachine the blades of the present invention is similar to that used in processing electronic integrated circuits. For example, FIG. 8 shows piezo-resistors 801 and 803 diffused on the blade 805 at the unsupported end 806 and near the handle 807, respectively for detecting forces that tend to bend the blade to one side or another. Metallization 809 connects piezo-resistors 801 and 803 to wiring 811. Wiring 811 may include a cable extending out of handle 807 and connected to a data acquisition and measurement module 813. When sufficient miniaturization is available and signal processing needs may be so met, wiring 811 and data acquisition and measurement module 813 may be entirely contained within handle 807. Data acquisition and measurement module 813 may further be connected to an optional computer control system 815 by interface 817.

In another embodiment, FIG. 9 illustrates a resistive heater 901 placed near the edge 201 of blade 903, thus enabling the surgeon to heat the cutting edge 201 to a desired temperature. This feature may facilitate a number of cutting procedures in which a heated cutting device facilitates tissue separation. This embodiment may also provide for cauterization and hemostasis along the cut surface during tissue separation. Sensors 905 may also be integrated onto the surface of blade 903. Temperature sensors on the blade could provide feedback regarding tissue temperature and condition. Other sensors could provide feedback regarding the force used during cutting of tissue segments. Metallization 907 connects resistive heater 901 and sensors 905 to wiring 909. As with wiring 811 of FIG. 8, wiring 909 may include a cable extending out of handle 807 and connected to a data acquisition and measurement module 911. The data acquisition and measurement module 911 of this embodiment may also further be connected to an optional computer control system 913 by interface 915.

In the embodiments of FIGS. 8 and 9, some functions of the data acquisition and measurement modules 813 and 911, respectively, may be integrated directly onto blades 805 and 903, respectively. This could be done using techniques known in the integrated circuit arts.

In use, the blade of the present invention is mounted in a holder, such as that illustrated in FIGS. 10–14. Such a holder allows safe manipulation of the blade, while supplying mechanical support to prevent breakage of the blade.

Figure 10:
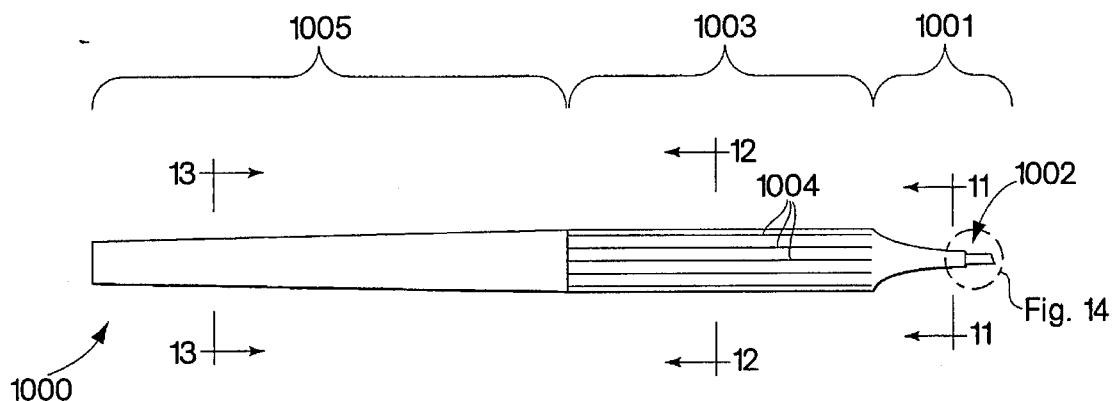
FIG. 10 is a side view of a blade holder suitable for use with blades of the present invention.

The blade holder 1000 of FIG. 10 may be a single injection molded unit, as shown. This unit has a tip region 1001 wherein a blade assembly 1002 is mounted. This embodiment includes a handle region 1003 having a plurality of ribs 1004. Ribs 1004 enable an operator to manipulate blade 1002 with greater accuracy, by providing blade holder 1000 with increased stiffness, lighter weight and better grip. Finally, the blade holder 1000 includes a tail section 1005, which acts as a counter-balance to tip region 1001.

Figure 11:
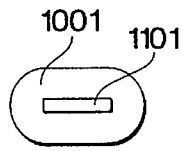
FIG. 11 is a cross-sectional view of the blade holder of FIG. 10, taken through line 11—11.

FIG. 11 shows a cross-sectional view of tip region 1001. In this view, there is a slot 1101 for receiving blade assembly 1002, located within the material of tip region 1001.

Figure 12:
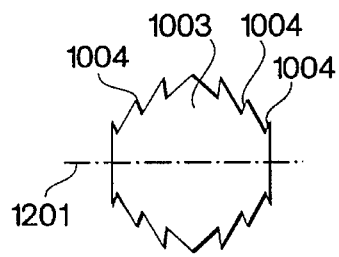
FIG. 12 is a cross-sectional view of the blade holder of FIG. 10, taken through line 12—12.

A cross-sectional view of handle region 1003 is found in FIG. 12. Handle region 1003 is symmetrical about center-line 1201. In FIG. 12, it may be seen that ribs 1004 are placed in suitable locations to stiffen blade holder 1000 and provide additional gripping area.

Figure 13:
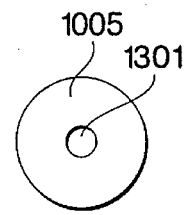
FIG. 13 is a cross-sectional view of the blade holder of FIG. 10, taken through line 13—13.

Tail region 1005 is shown in cross-section in FIG. 13. As seen in FIG. 13, tail section 1005 may be provided with a weighted core 1301, for example a steel rod, for giving blade holder 1000 a desired heft and balance.

Figure 14:
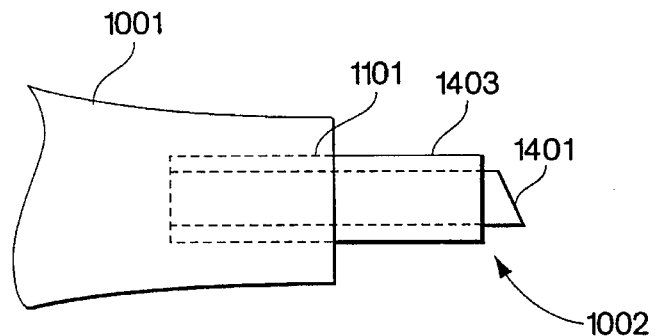
FIG. 14 is a detailed view of the attachment of a blade to the blade holder of FIG. 10, taken at the region denoted 14 in FIG. 10.

FIG. 14 illustrates the details of attaching blade assembly 1002 to tip region 1001. Blade assembly 1002 is inserted into slot 1101, wherein it may be held by adhesive means or interference fit, for example. As shown in FIG. 14, blade assembly 1002 may include both a blade 1401 and a sleeve 1403 (e.g., of metal). Sleeve 1403 provides additional support for blade 1401, such that any tendency of blade 1401 to fracture under bending stress may be reduced. With this arrangement, even if blade 1401 should fracture, sleeve 1403 would retain the broken portion in the holder. However, where sleeve 1403 is undesirable for a particular application, a bare blade 1401 may be fastened into slot 1101.

Figure 15:
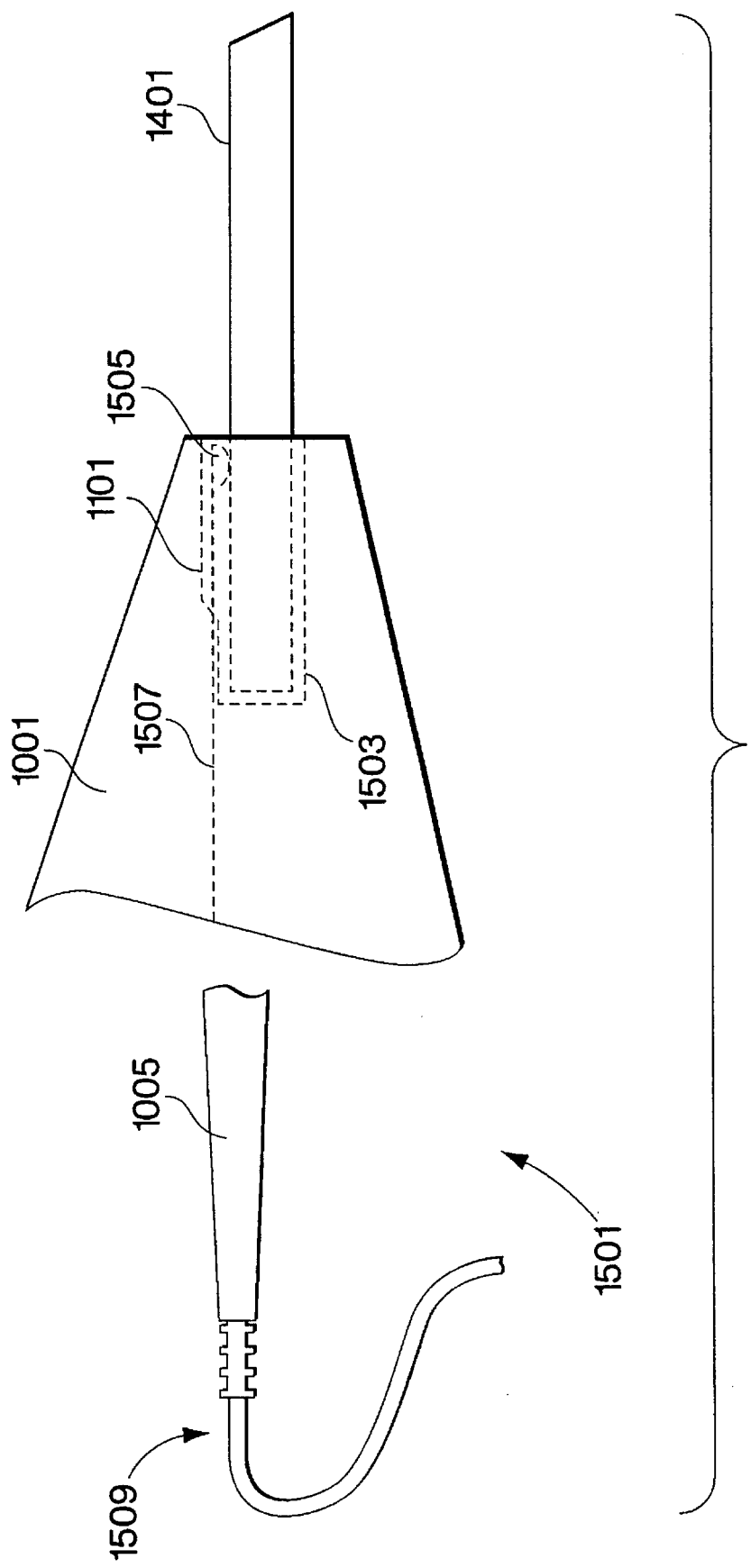
FIG. 15 is a combination view illustrating an electronically assisted cutting instrument.

An electronically assisted cutting instrument, such as shown in FIG. 15, may include the blade of FIG. 8 or FIG. 9. Blade 1401 is inserted into slot 1101 in tip region 1001 of a blade holder 1501. Slot 1101 may be tapered at one end 1503 to firmly capture the inserted portion of blade 1401. Near the entry of slot 1101 may be one or more springy conductors 1505, positioned for electrical engagement with corresponding contact pads on blade 1401. Springy conductors 1505 lead back through the body of blade holder 1501, possibly forming or connected to embedded conductors 1507. Embedded conductors exit the tail 1005 of blade holder 1501, to form cable 1509.

Use of blades according to the present invention is now described with reference to FIGS. 16–20. These Figs. illustrate several cuts made using conventional blades and using blades according to the present invention. Each cut is perpendicular to the surface of the tissue, approximately 4–5 mm long and approximately 3–4 mm deep.

Blades according to the present invention cleave biological tissues with less distortion of the internal structure of the cut tissues than conventionally sharpened blades. A smooth blade cutting surface and low edge radius contribute to less drag during use. Tissue segments are thus separated with minimal disruption. Less separation of tissue planes during surgical manipulation result in decreased tissue reaction and less scar tissue formation. Decreased trauma to tissue and increased precision in procedure performance generally contribute to improved healing.

Figure 16:
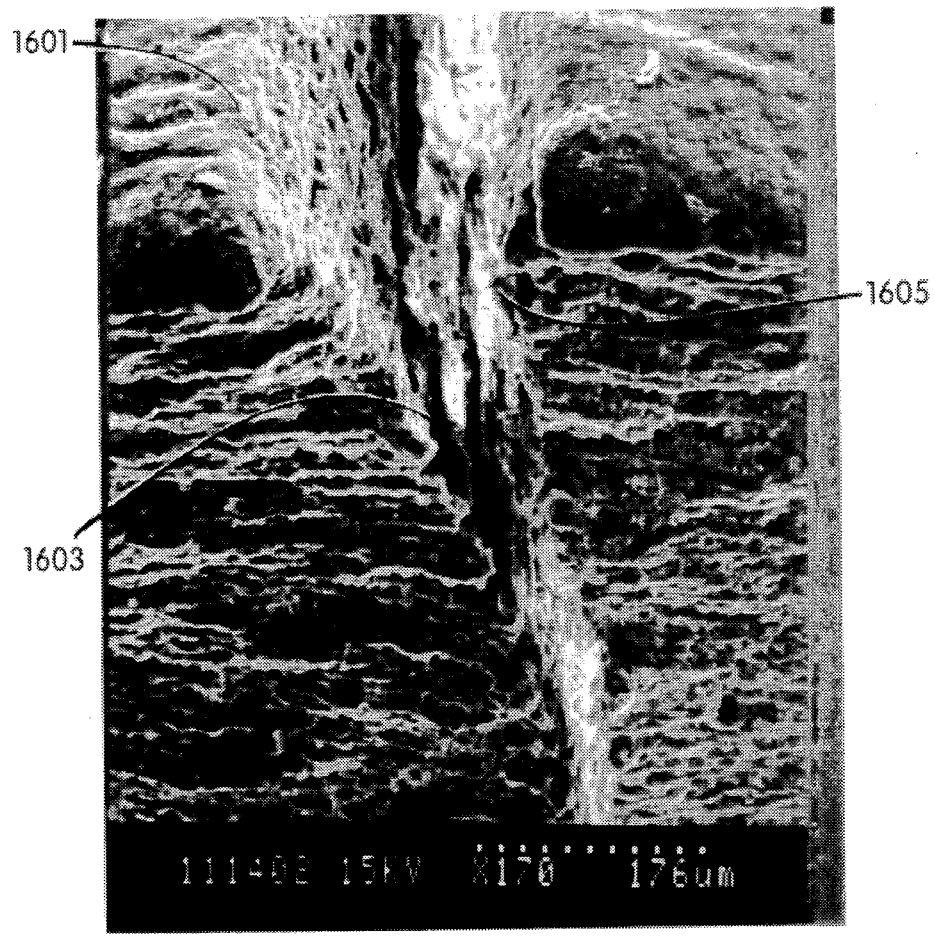

FIG. 16 is a cross sectional scanning electron micrograph of a cut made in fresh artery tissue using a conventional surgical blade. Gross irregularities may be seen along the contact surface 1601 with separation and distortion of tissue layers (e.g. 1603 and 1605) along the depth of the incision which results from high friction and the large force needed to separate tissue during cutting, and irregularities in the blade surface construction.

Figure 17:
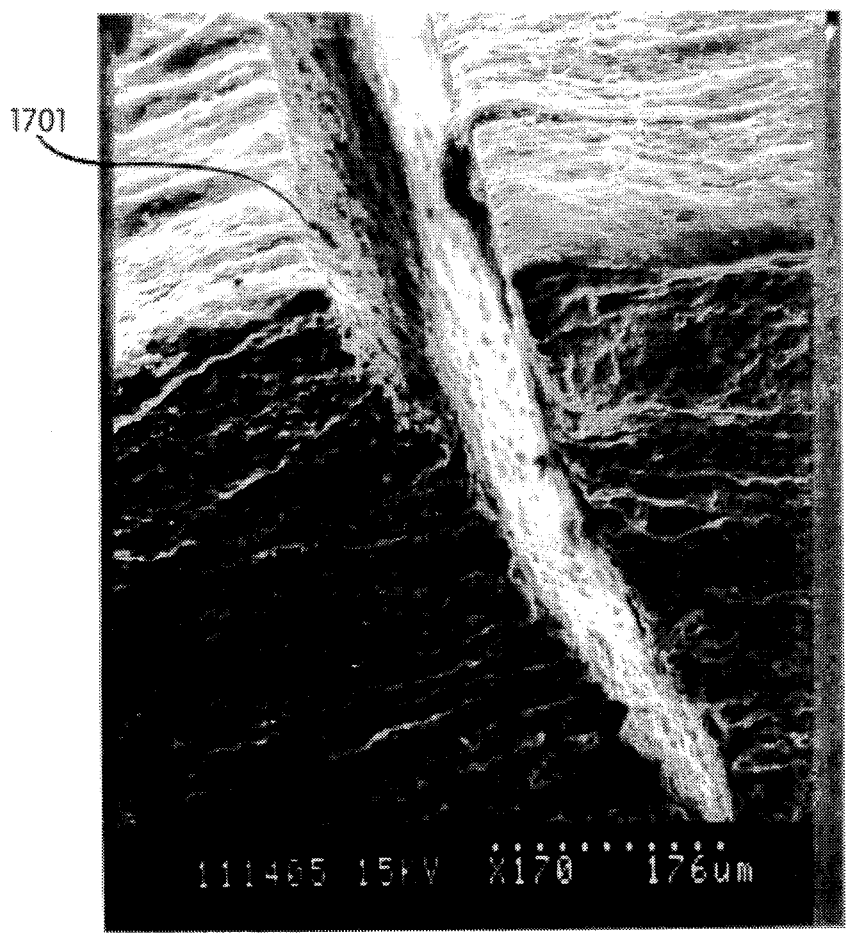

In contrast, FIG. 17 is a cross sectional scanning electron micrograph of a cut made in fresh artery tissue, using a blade according to the present invention. The contact surface 1701 demonstrates a smoother more accurate edge. The cut surface, as well, is remarkable for minimally detectible distortion or distraction of tissue layers from the blade activity. Less tissue debris is seen along the cut surface when compared to FIG. 16, due to the smooth nature of the blade surfaces which contact the tissue after the initial tip cleaving action has occurred.

Figure 18:
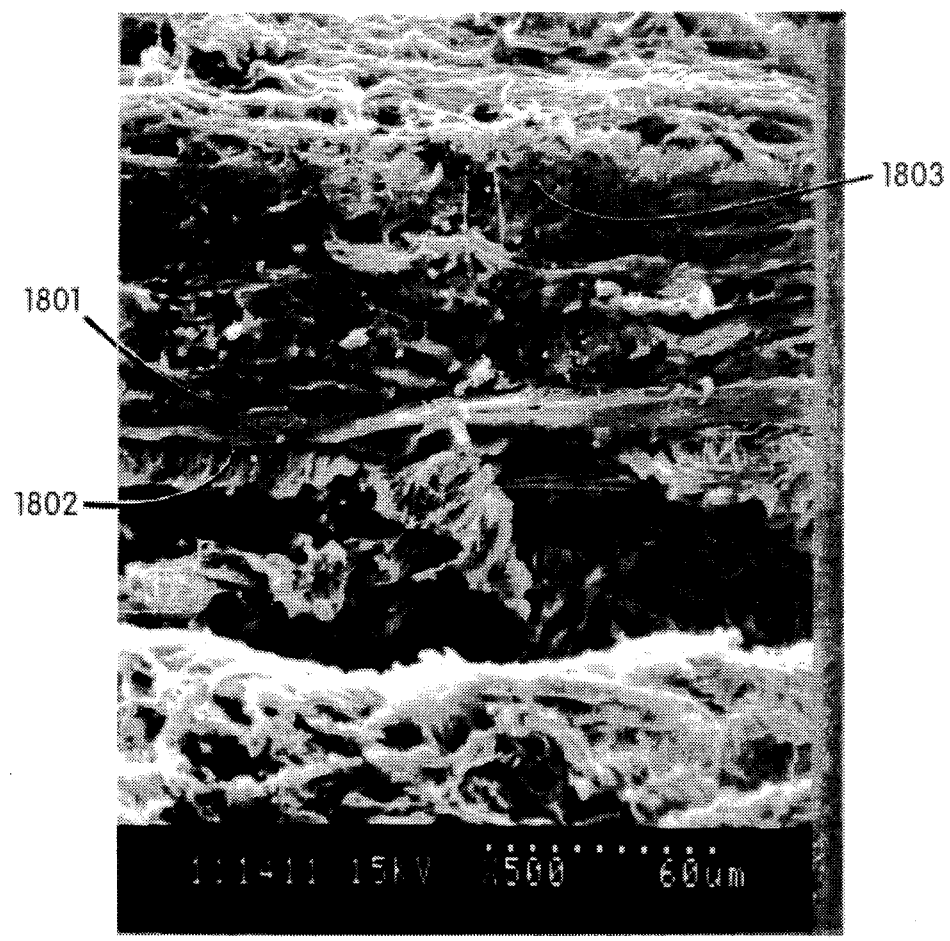
Figure 19:
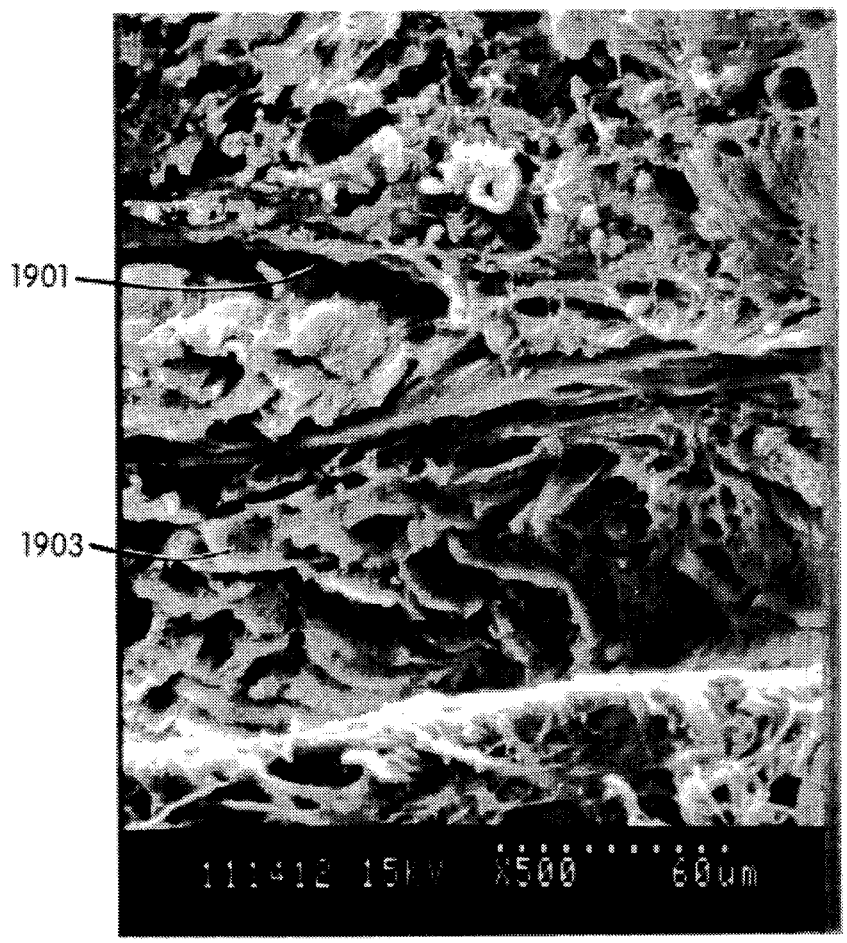
Figure 20:
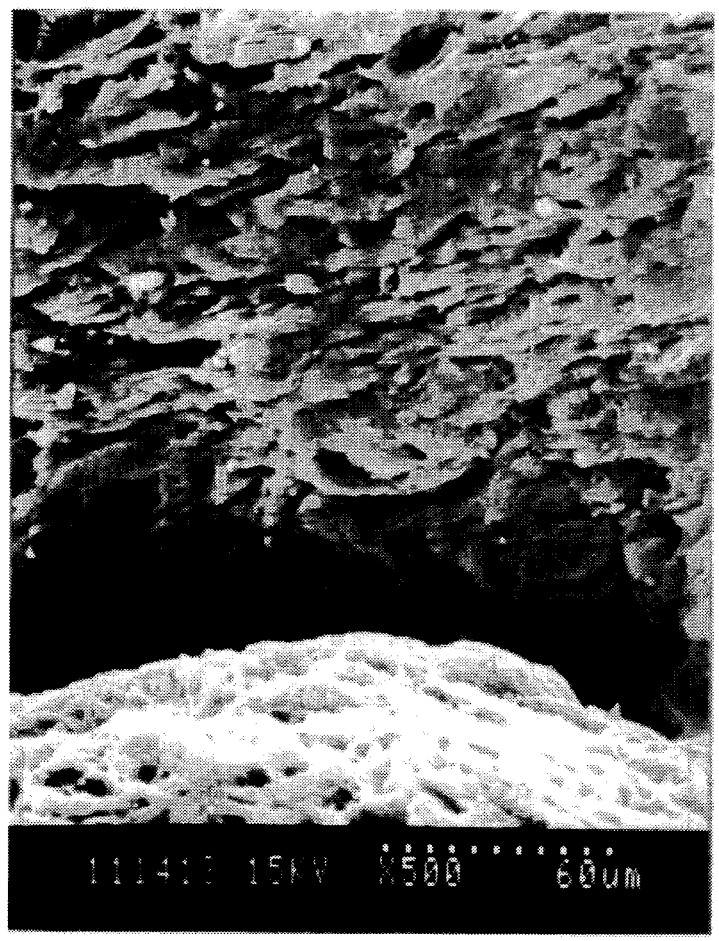

FIGS. 18, 19 and 20 represent scanning electron micrographs of the inside surface of cuts made in bovine sclera tissue. FIG. 18 is a cut made with a conventional stainless steel surgical blade. FIG. 19 is a cut made with a specialty ophthalmology blade. FIG. 20 is a cut made with a surgical blade according to the present invention. Significant differences in tissue disruption may be observed in these electron micrographs. In FIG. 18, large fragments of tissue (e.g., 1801, 1802 and 1803) are disrupted, distorting the normal architecture of the structure, irregular contour 1801, fragments of tissue 1802 and debris 1803, which contribute to increased tissue damage and probability of tissue necrosis and scar formation. FIG. 19 demonstrates less tissue disruption resulting from a more defined cutting edge. Modest distortion 1901 of tissue planes is evident with less separation of planes 1903 noted. FIG. 20 represents a cut made with a blade according to the present invention and demonstrates significantly less distortion of tissue planes, minimal disturbance of the normal architecture and clean cleavage of tissue components. Less trauma to the tissue contributes to a lower probability of tissue necrosis, scar formation or unacceptable results.

The invention has now been described in connection with a number of particular embodiments and illustrations. The particular embodiments and illustrations are provided by way of example only. Many variations and modifications to these embodiments would be obvious to those skilled in the art. Such variations and modifications are contemplated as falling within the scope of the present invention, which is limited only by the appended claims.

What is claimed is:

1. A micromachined cutting blade, comprising
   a body of silicon having a sharp cutting edge, including at least one segment defined by an intersection of two crystal planes;
   wherein the body of silicon is a single-crystal wafer; and further comprising
   an electronic circuit element diffused into a surface the silicon wafer, and non-electrically coupled to the silicon wafer.

2. A blade, as recited in claim 1, wherein the cutting edge of the body includes a plurality of the segments.

3. A micromachined blade as recited in claim 1, suitable for surgical use and further comprising:
   a sharp tip formed by an intersection of a third crystal plane and the intersection of two crystal planes.

4. A blade, as recited in claim 1, wherein the body has a bottom surface adjacent the cutting edge, the bottom surface substantially corresponding with a <100> plane of the silicon.

5. A blade, as recited in claim 1, wherein the cutting edge substantially corresponds with a <111> plane of the silicon.

6. A blade as recited in claim 1, wherein the electronic circuit element includes a strain/stress sensor.

7. A blade, as recited in claim 1, wherein the electronic circuit element includes a resistive heater.

8. A cutting instrument, comprising:
   a micromachined blade having a sharp cutting edge including at least one segment defined by an intersection of two crystal planes;
   a handle having a slot at one end, into which the micromachined blade is inserted;
   electronic circuitry integrated into a surface of the micromachined blade, including contact pads for making electrical contact with the electronic circuitry; and
   means for making electrical contact with the contact pads, the means disposed within the slot in the handle.

* * * * *